(12) United States Patent
Danenberg et al.

(10) Patent No.: US 9,005,158 B2
(45) Date of Patent: Apr. 14, 2015

(54) ERADICATION OF PIGMENTATION AND SCAR TISSUE

(75) Inventors: Noam Danenberg, Hod Hasharon (IL); Ori Nesher, Herzliya (IL)

(73) Assignee: Hawk Medical Technologies Ltd., Ra'Anana (IL)

( * ) Notice: Subject to any disclaimer, the term of this patent is extended or adjusted under 35 U.S.C. 154(b) by 1894 days.

(21) Appl. No.: 11/997,411

(22) PCT Filed: Jul. 27, 2006

(86) PCT No.: PCT/IL2006/000876
§ 371 (c)(1),
(2), (4) Date: Mar. 4, 2008

(87) PCT Pub. No.: WO2007/015232
PCT Pub. Date: Feb. 8, 2007

(65) Prior Publication Data
US 2008/0221548 A1    Sep. 11, 2008

(30) Foreign Application Priority Data
Aug. 1, 2005    (IL) .......................................... 170020

(51) Int. Cl.
*A61B 17/20* (2006.01)
*A61Q 19/00* (2006.01)
(Continued)

(52) U.S. Cl.
CPC ................ *A61Q 19/00* (2013.01); *A61K 8/368* (2013.01); *A61M 37/0076* (2013.01);
(Continued)

(58) Field of Classification Search
CPC .......... A61M 37/0016; A61M 1/0058; A61M 2037/0007; A61M 2037/0023; A61M 2037/0046; A61M 2037/0061; A61M 2205/05

USPC ......... 604/46, 22, 27, 28, 173, 268, 289, 290; 81/9.22
See application file for complete search history.

(56) References Cited

U.S. PATENT DOCUMENTS 4,588,400 A    5/1986    Ring et al.
4,665,063 A    5/1987    Bar-Shalom
(Continued)

FOREIGN PATENT DOCUMENTS

CA    1283099    4/1991
EP    0576279    12/1993
(Continued)

OTHER PUBLICATIONS
International Search Report PCT/IL2006/000876.
(Continued)

*Primary Examiner* — Aarti B Berdichevsky
*Assistant Examiner* — Laura Schell
(74) *Attorney, Agent, or Firm* — Fleit Gibbons Gutman Bongini & Bianco PL; Martin Fleit; Paul D. Bianco

(57) ABSTRACT

The invention is a non-surgical method for the eradication of pigmentation and scar tissue from an area of skin. The method comprises repeatedly puncturing the area of skin with an array of needles. As the needles are inserted into the skin, the needles and surface of the skin are washed with a clean solution. As the needles are withdrawn from the skin, the flow of clean solution ceases and the dirty solution, which contains cellular fluids and pigments released by the action of the needles, is removed from the surface. The invention is also a solution, which is used to clean the needles and to aid in destroying the pigment containing cells, and an apparatus, which is especially designed to move the needles into and out of the surface of the skin and to provide synchronization of the motion of the needles and flow of the solution such as to maximize the effectiveness of the method.

18 Claims, 5 Drawing Sheets

(51) Int. Cl.
*A61K 8/368* (2006.01)
*A61M 37/00* (2006.01)
*A61Q 19/02* (2006.01)
*A61B 17/00* (2006.01)

(52) U.S. Cl.
CPC .............. *A61Q 19/02* (2013.01); *A61B 17/205* (2013.01); *A61B 2017/00747* (2013.01); *A61B 2017/00756* (2013.01); *A61B 2017/00761* (2013.01); *A61B 2017/00769* (2013.01)

(56) References Cited

U.S. PATENT DOCUMENTS

| | | | |
|---|---|---|---|
| 4,788,146 | A | 11/1988 | Ring |
| 4,858,604 | A | 8/1989 | Konishi |
| 5,019,596 | A | 5/1991 | Reiner et al. |
| 5,244,920 | A | 9/1993 | Reiner et al. |
| 5,271,943 | A | 12/1993 | Bogart et al. |
| 5,401,242 | A | 3/1995 | Yacowitz |
| 5,423,736 | A | 6/1995 | Cartmell et al. |
| 5,562,643 | A * | 10/1996 | Johnson .................. 604/290 |
| 5,714,225 | A | 2/1998 | Hansen et al. |
| 6,083,196 | A | 7/2000 | Trautman et al. |
| 6,251,121 | B1 | 6/2001 | Saadat |
| 6,375,977 | B1 | 4/2002 | Auguste et al. |
| 6,432,114 | B1 | 8/2002 | Rosso |
| 6,485,714 | B1 | 11/2002 | Mangione et al. |
| 6,607,513 | B1 | 8/2003 | Down et al. |
| 6,689,095 | B1 | 2/2004 | Garitano et al. |
| 6,692,456 | B1 | 2/2004 | Eppstein et al. |
| 6,743,211 | B1 | 6/2004 | Prausnitz et al. |
| 6,890,319 | B1 | 5/2005 | Crocker |
| 7,012,096 | B2 | 3/2006 | Dosch et al. |
| 7,314,470 | B2 | 1/2008 | Malodobry |
| 7,658,742 | B2 | 2/2010 | Karasiuk |
| 7,905,854 | B2 | 3/2011 | Hazut et al. |
| 7,951,156 | B2 | 5/2011 | Karasiuk |
| 2002/0013300 | A1* | 1/2002 | Capelli-Schellpfeffer ... 514/159 |
| 2002/0138049 | A1 | 9/2002 | Allen et al. |
| 2002/0183688 | A1 | 12/2002 | Lastovich et al. |
| 2003/0212415 | A1 | 11/2003 | Karasiuk |
| 2004/0001878 | A1 | 1/2004 | DeBusk et al. |
| 2004/0111107 | A1 | 6/2004 | Malodobry |
| 2004/0158196 | A1 | 8/2004 | Garitano et al. |
| 2005/0065463 | A1 | 3/2005 | Tobinaga et al. |
| 2006/0142708 | A1 | 6/2006 | Hazut et al. |
| 2007/0088371 | A1 | 4/2007 | Karasiuk |
| 2007/0156095 | A1 | 7/2007 | Hazut et al. |
| 2008/0031288 | A1 | 2/2008 | Sierra |
| 2008/0208235 | A1 | 8/2008 | Ulmer et al. |
| 2008/0221548 | A1 | 9/2008 | Danenberg et al. |
| 2012/0136374 | A1 | 5/2012 | Karasiuk |
| 2012/0179134 | A1 | 7/2012 | Garitano et al. |

FOREIGN PATENT DOCUMENTS

| | | | |
|---|---|---|---|
| EP | 0762860 | B1 | 12/1997 |
| GB | 840289 | | 6/1958 |
| GB | 2234420 | | 2/1991 |
| JP | 06-065060 | | 3/1994 |
| JP | 2001-293095 | | 10/2001 |
| JP | 2001293095 | A | 10/2001 |
| RU | 2173983 | | 11/2000 |
| RU | 2173983 | | 9/2001 |
| WO | 9106323 | A1 | 5/1991 |
| WO | 93/10731 | | 6/1993 |
| WO | 96/21410 | | 7/1996 |
| WO | 99/64580 | | 12/1999 |
| WO | 0064514 | A1 | 11/2000 |
| WO | 00/76411 | | 12/2000 |
| WO | 01/91697 | | 12/2001 |
| WO | 0236027 | A2 | 5/2002 |
| WO | 2004082469 | A2 | 9/2004 |
| WO | 2004/107995 | | 12/2004 |
| WO | WO 2004/107995 | A2 | 12/2004 |
| WO | WO 2005/020828 | * | 2/2005 ............ A61B 17/20 |
| WO | WO 2005020828 | * | 2/2005 ............ A61B 17/20 |
| WO | 2005/020828 | | 3/2005 |
| WO | 2005020828 | A1 | 3/2005 |
| WO | WO 2005/020828 | A1 | 3/2005 |

OTHER PUBLICATIONS

International Preliminary Report on Patentability PCT/IL2006/000876.
International Search Report published Feb. 8, 2007 for PCT/IL2006/000876 filed Jul. 27, 2006.
International Preliminary Report on Patentability published Feb. 5, 2008 for PCT/IL2006/000876 filed Jul. 27, 2006.
Written Opinion published Feb. 1, 2008 for PCT/IL2006/000876 filed Jul. 27, 2006.
International Preliminary Report on Patentability (chapter II) published Mar. 27, 2009 for PCT/IL2006/000876 filed Jul. 27, 2006.
Mashkovsky MD, Therapeutic Agents, vol. 2, M. Meditsina publishers, 1993, p. 455-56.
Swinehart JM, Salicylcic acid ointment peeing of the hands and forearms, Effective Nonsurgical Removal of Pigmented Lesions and Actinic Damage, J. Dermatol. Surg Oncol Jun. 18, 1992 (6) p. 495-8, abstract.
Tattoo Removal,.http://patient-info.com/tattoo/htm. copyright 2000. p. 3, Salabrasion.
Swinehart JM, Salicyclic acid ointment peeling of the hands and forearms. Effective nonsurgical removal of pigmented lesions and actinic damage, J Dermatol Surg Oncol. Jun. 1992; 18(6): 495-8, abstract.
www.healthylivinganswers.com/skin-care/, Feb. 26, 2010m layers of the skin-epidermis-dermis-hypodermis.
Gary H. Manchester Tattoo removal a new simple technique, California medicine, 1973, 118,3,10%12).
Tattoo removal: tannic acid method of Variot, E.B. Walle et al., International Journal of Dermatology, 1993,32,5,376-380).
Takesue, M , Aichi Gakuin Daigaku Shigakkai Shi, 27 (1):277%316, 1989, Effect of Caffeine on Wound Healing of the Rat Gingiva, abstract.
Eddy M. Van Der Velden at al. Tattoo Removal: Tannic Acid Method of Variot, Pharmacology & Therapeutics, pp. 376-380, vol. 5 (5), May 1993.
Taylor CR, Anderson RR, Gange RW, Michaud NA, Flotte TJ, Light and electron microscopic analysis of tattoos treated by Q-switched ruby laser. Journal of Investigative Dermatology. vol. 97, No. 1, pp. 131%136, Jul. 1991.
An abstract of the article: Lea P.J., and Pawlowski A., Human tattoo. Electron microscopic assessment of epidermis, epidermal-dermal junction, and dermis, Int J Dermatol Sep. 1987: 26(7): 453%8.
Page 2508 from chapter 267, Lasers in Dermtology. by Graeme M. Lipper and R. Rox Anderson in: Fitzpatrick's, Dermatoloay in General Medicine, sixth edition, 2003.
Material Safety Data Sheet (MSDS) for Sodium chloride ACS Reagent sold by Sigma-Aldrich, Feb. 1, 2006.
Material Safety Data Sheet (MSDS) for RNase-Free Buffer (5M NaCl)sold by Ambion, Inc. Jan 10, 2006.
USPTO documents for U.S. Appl. No. 10/560,063 including Final rejection (dated Nov. 1, 2011); amendment (Aug. 8, 2011); non-final rejection (Feb. 15, 2011); amendment (Jan. 20, 2011); final rejection Jul. 20, 2010); amendment (Apr. 26, 2010); final rejection (Oct. 26, 2009); amendment (Sep. 16, 2009); examiner interview (Jun. 29, 2009); amendment (Jun. 24, 2009); amendment (May 18, 2009); final rejection (Mar. 16, 2009).
USPTO documents for U.S. Appl. No. 10/560,063 including amendment (dated Feb. 24, 2009); final rejection (Dec. 24, 2008); amendment (Sep. 16, 2008); amendment (Apr. 16, 2008); amendment (Jan. 18, 2006); advisory action (Dec. 27, 2007); amendment (Dec. 28, 2007); advisory action (Dec. 27, 2007); amendment (Dec. 18, 2007); final rejection (Oct. 18, 2007); amendment (Jun. 26, 2007); office action (Feb. 26, 2007).
For U.S. Appl. No. 10/560,063: Notice of Appeal Filed (dated May 1, 2012); Appeal Brief filed with affidavit (Aug. 29, 2012) Examiner's answer to appeal brief (Dec. 19, 2012); Reply Brief Filed (Feb. 17, 2012); Appealing Docketing Notice (Feb. 28, 2013).

* cited by examiner

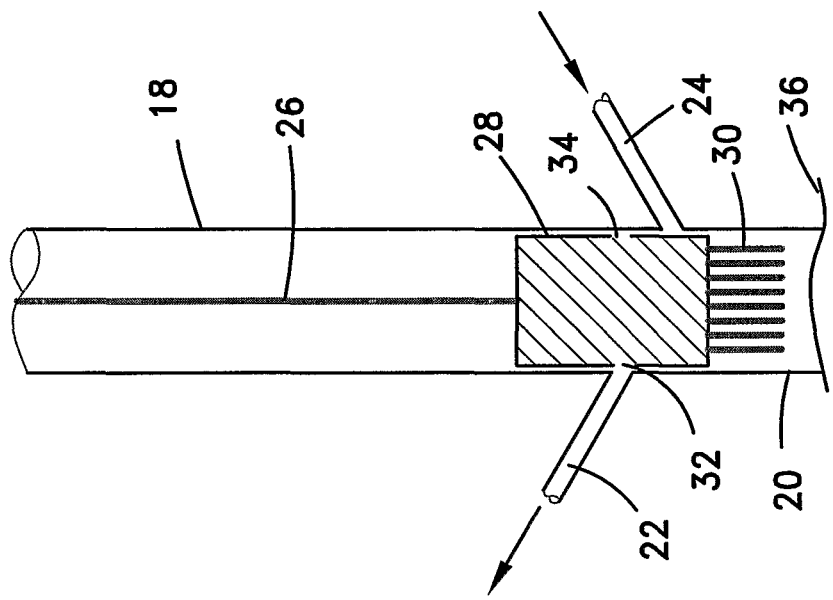
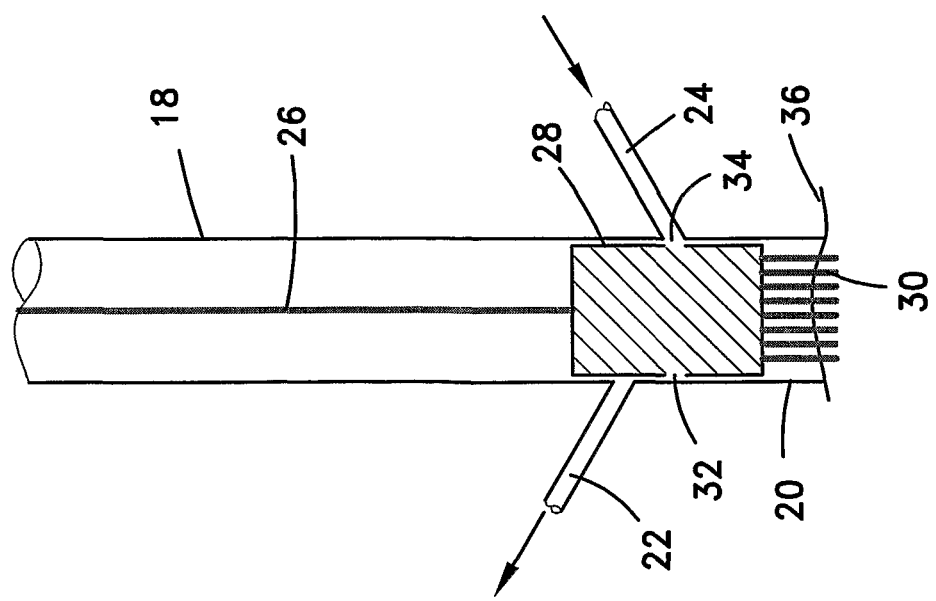

ERADICATION OF PIGMENTATION AND SCAR TISSUE

FIELD OF THE INVENTION

The present invention relates to the field of cosmetic treatments. Specifically the present invention relates to the non-surgical eradication of pigmentation and scar tissue from an area of skin.

BACKGROUND OF THE INVENTION

Pigmented areas of skin can be either intentionally created, e.g. by tattooing or the result of natural processes, such as the healing of wounds, freckles, age spots, birth marks, etc. For cosmetic or a variety of other reasons, people often wish to have a pigmented area removed from their skin. Topical ointments are often used to try to treat the cause of the pigmentation or to cover it up. However, because the pigment is an integral part of the cells in the dermis, removing the pigmentation is not an easy task and can only be effectively accomplished by destroying and replacing the cells containing the pigment. Known methods of eradicating pigmentation include:

Dermabrasion, wherein skin is "sanded" (i.e., abraded) to remove the layers of skin containing the pigmentation;

Cryosurgery, wherein the pigmented area is frozen prior to its removal; and

Excision, wherein a dermatologic surgeon removes the pigmented skin with a scalpel and closes the wound with stitches. In some cases involving large areas of skin, a skin graft from another part of the body may be necessary.

These methods are typically quite painful and frequently leave white spots and occasionally scars.

Lasers offer a more precise and generally less damaging alternative to the abovementioned methods. Each procedure is done as a single treatment, or in a series of treatments. Patients may or may not require topical or local anesthesia. Lasers remove the pigment by producing short pulses of intense light, which pass through the top layers of the skin and are then selectively absorbed by the pigment. The laser energy causes the pigment to be fragmented into smaller particles, which are then removed by the body's immune system. One of the problems with laser treatment, especially for the removal of tattoos, is that the absorption of the laser energy is color dependent and that a given laser can only be used to remove pigments in a particular color range. Moreover, there are side effects of laser procedures including occasional burning, scaring, hyper pigmentation (an abundance of color in the skin at the treatment site) and hypo pigmentation (the treated area lacks normal skin color).

Less traumatic methods for removing pigmented areas of skin are described in International Patent Applications WO2004/107995 and WO2005/020828 by the Applicant of the present application, the descriptions of which, including reference cited therein, are incorporated herein by reference in their entirety. According to the methods described in these publications, the pigmented area of skin is repeatedly punctured by an array of needles attached to a tattooing machine, or similar device. In the method described in the first application, after the skin is punctured by the needles for a given period of time, the punctured section is covered with a suitable adsorbing pad. The pad contains one or more materials, such as saline, which help the pigments that are released from the interior of the damaged cells at the punctured section to migrate into the outer layer of the skin and be absorbed in the pad. The device described in the second application comprises a mediating member attached to a machine and used for repeatedly puncturing the skin. The mediating member is in contact with the skin and provides means for drawing off the cellular fluids and pigments which rise to the skin surface at the site of the punctured skin and for washing the needles and surface of the skin with a suitable liquid if desired.

Another cosmetic problem is scar tissue, which forms when skin tissue heals after an injury. Surgical procedures can be used to remove scar tissue and the application of topical medications can sometimes be used to restore scar tissue to a more natural color and texture. There is need for a procedure for removing scar tissue that avoids the possible risks and complications of surgery, provides complete healing of the skin, and gives faster results than both surgical procedures and treatment with medication.

It is a purpose of the present invention to provide a method for complete eradication of pigmentation and scar tissue that overcomes the limitations of the prior art methods.

Further purposes and advantages of this invention will appear as the description proceeds.

SUMMARY OF THE INVENTION

In a first aspect the invention is the use of salicylic acid for the eradication of scar tissue and pigmentation in an area of skin. The salicylic acid, which is applied to the area of skin is in an aqueous solution at a concentration below that which will be toxic if the solution enters the bloodstream.

In a preferred embodiment the area of skin is repeatedly punctured while the salicylic acid is applied. The puncturing can be done using an array of needles. The solution flows onto the needles rinsing them each time the skin is punctured.

In a preferred embodiment the concentration of salicylic acid is between 2% and 5%. The pigmentation can be from a tattoo or due to a natural process, e.g., healing of wounds, freckles, age spots, or birth marks.

In another aspect, the invention is an apparatus for eradicating scar tissue and pigmentation from an area of skin. The apparatus comprises:

(a) a handle section comprising a motor and gear assembly for causing a reciprocating motion to a shaft connected to the gear assembly;

(b) a barrel section surrounding the shaft, the first end of the tubular element attached to the skin puncturing device and having a tip adapted to form a hermetic seal with the skin;

(c) an array of needles attached to the shaft near the tip;

(d) a piston attached to the shaft above the array of needles, the piston providing a hydraulic seal that separates the volume inside the barrel section above the piston from the volume below it;

(e) an exit port in the barrel, the exit port connected to suction means; and (f) an entrance port in the barrel, the entrance port connected to solution storage means.

The apparatus of the invention is characterized in that when the motor is activated, the array of needles is caused to alternately be pushed out of the tip to puncture the area of skin, thereby mechanically damaging the cells in the dermis containing the pigments, and to be withdrawn from the area of skin back into the tip. During each downward stroke of the shaft the exit port is closed, the entrance port is opened, and solution contained in the solution storage means flows onto the needles rinsing them and onto the surface of said area of skin. During each upward stroke the entrance port is closed, the exit port is opened, and the solution, which flowed onto the surface of the area of skin during the downward stroke, and the cellular fluids and the pigments released by the action of said needles are sucked out of the barrel by the suction means. Synchronization of the opening and closing of the inlet and outlet means in this manner insures that there is an absolute separation between the clean and dirty fluid in the tip, that the needles that penetrate the skin are always clean, and minimizes the amount of fluid that permeates into the dermis.

In a preferred embodiment of the apparatus of the invention the piston is a specially designed cylindrical valve.

In another aspect the invention is a method of using a skin puncturing apparatus of the invention to eradicate scar tissue and pigmentation from an area of skin. The method comprises:

(a) providing a solution in the solution storage means;
(b) connecting the solution storage means and suction means to the apparatus; and
(c) activating the motor and of the apparatus for a predetermined period of time.

The solution is of a chemical, which can be selected from the group comprising: EDTA, DMSO, Collagenase, Hyaluronidase, Papain, Bromelain hypertonic Saline, Salicylic Acid, *Aloe, Bidentis, Kalanchoes, Eucalyptus*, Chamomile, *Calendula, Salvia oficinalis, Helichrysum arenarium*, and Hydrogen Peroxide.

In a preferred embodiment of the method of the invention the solution is an aqueous solution of salicylic acid at a concentration of between 2% and 5%.

All the above and other characteristics and advantages of the invention will be further understood through the following illustrative and non-limitative description of preferred embodiments thereof, with reference to the appended drawings.

BRIEF DESCRIPTION OF THE DRAWINGS

FIG. 2A and FIG. 2B are schematic cross-sectional views of the barrel portion of the apparatus shown in FIG. 1;

DETAILED DESCRIPTION OF PREFERRED EMBODIMENTS

The present invention is the result of work done by the inventors to improve the results of the cosmetic treatment obtained by using the apparatus and method described in the above mentioned international patent applications. The search for improvements was in all aspects of the treatment including: reducing the time of treatment, reducing the period of time between the end of a treatment and the time when acceptable visible results were obtained, reducing the expense of the treatment, and minimizing the difference between the color of the formally pigmented area and the natural skin color.

The basic design and operation of the apparatus have been previously described. However, certain improvements, which will be described hereinbelow, have been made to the apparatus in order to increase the efficiency of its operation. The largest improvements in the treatment results have resulted from the type of solution and the method of applying it to the surface of the area being treated. Many different solutions were considered including EDTA, DMSO, Collagenase, Hyaluronidase, Papain, Bromelain hypertonic Saline, Salicylic Acid, *Aloe, Bidentis, Kalanchoes, Eucalyptus*, Chamomile, *Calendula, Salvia oficinalis, Helichrysum arenarium*, and Hydrogen Peroxide. Of these EDTA, DMSO, Salicylic Acid, Hydrogen Peroxide, and hypertonic solutions of sodium chloride were selected for further testing at this time. As a result of their preliminary experiments, the inventors have found that that the combination of repeatedly puncturing the skin, in order to mechanically destroy the cells containing the pigment, in the manner described hereinbelow together with rinsing the pigmented area with an aqueous solution of salicylic acid gives excellent results in eradicating pigments. Furthermore, it has been found that the same method, when applied to scar tissue is effective in removing the scar tissue and replacing it with healthy skin.

In the experiments performed to date, an aqueous solution containing between 2% and 5% of salicylic acid have been used. Although the solution is only applied to the surface of the skin and is not injected directly into the cells containing the pigments, it is apparent that some of it permeates through the holes made by the needles, reaches the area surrounding the cells and assists the needles to damage the cells inside the dermis. Further toxicological tests will be carried out in the future to determine the upper limit of concentration vs. time of treatment that can safely be used with humans. It has been found that only in special cases has it been felt necessary to lightly bandage the treated areas for a short while to keep the area clean. It might be that in some cases applying a pad as described in the above referenced WO2004/107995-rill improve the results of the treatment described herein.

Figure 1:
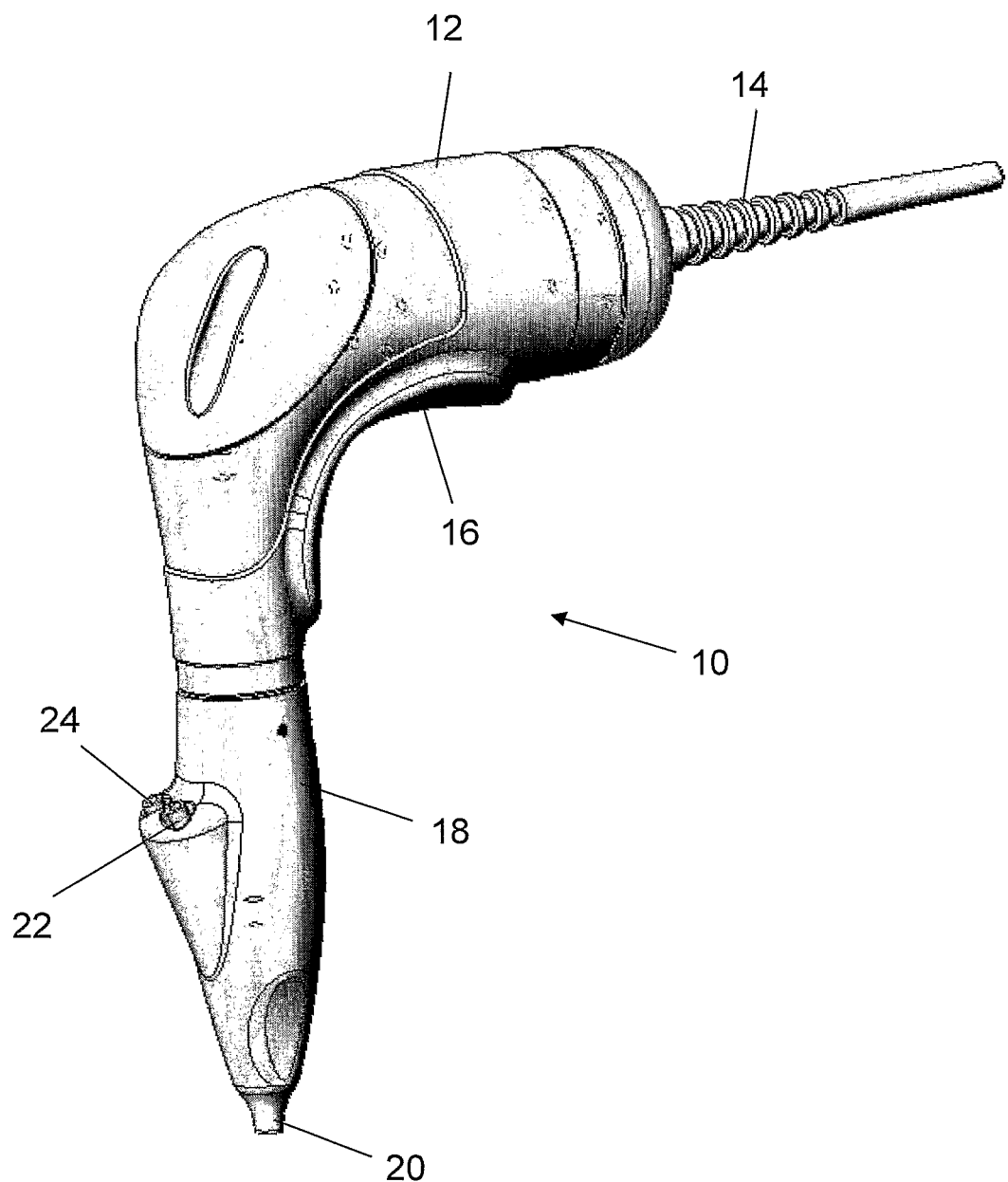
FIG. 1 shows the apparatus of the invention.

FIG. 1 shows an external view of the apparatus 10 of the invention. As said hereinabove and described in the two above referenced International Patent Applications, the apparatus of the invention is very similar in many ways to a conventional tattooing machine. For easy handling, the apparatus 10 is shaped like a pistol comprising handle section 12, barrel section 18, and a trigger 16 to activate the apparatus.

Inside handle 12 is a motor that is connected to a shaft inside of barrel section 18 of the device through a gear assembly. When rotated by the motor, the gears impart a reciprocating motion to the shaft; thereby causing the shaft to move back and forth inside the barrel. The power source can be batteries, either external or internal or an external source of electricity, e.g. a transformer that delivers a current of 0 to 1 amperes at 6 to 12 volts, through power cord 14.

Also seen in FIG. 1 are the tip 20 of the barrel, outlet port 22, and inlet port 24. Tip 20 is shaped so that when it is pressed against the skin a hermetic seal is created isolating the interior of the barrel from the outside. Ports 22 and 24 are connected respectively to a source of suction and a fluid supply container (neither of which are shown in the figures or described in detail herein).

FIG. 2A and FIG. 2B are schematic cross-sectional views showing the interior of barrel portion 18 of apparatus 10. These figures have been greatly simplified and the locations of some of the parts rearranged in order to more easily describe the operation of the apparatus. Fixedly attached to shaft 26 are cylindrical valve 28 and array of needles 30. As the shaft 26 is moved up and down by the motor, the array of needles 30 is alternately pushed through the outer layer of skin 36 into the dermis and withdrawn from the skin into the tip 20 of barrel 18.

The number of needles in the array depends on, amongst other factors, the size of the apparatus. A typical array can comprise, for example, between 7 to 38 needles. The apparatus is designed such that when the piston 26 is at it lowest position, the needles extend through tip 20 and penetrate the skin to a depth of between 0 to 3 mm, the exact depth depending on the location of the area to be treated and determined such that the tips of the needles do not pass through the dermis into the underlying fatty layer.

Cylindrical valve 28 is essentially a cylindrically shaped piston that provides a hydraulic seal that separates the volume inside the barrel 18 above valve 28 from the volume below it. Valve 28 has two openings, inlet hole 34 and outlet hole 32, in its side wall. Both of these openings are fluidly connected to the bottom of valve 28, such that fluid in the fluid supply container can alternately flow through inlet port 24 and inlet hole 34 in order to wash the needles and skin surface and be sucked out of the tip 20 of the barrel 18 through outlet hole 32 and outlet port 22. The function of the cylindrical valve is to insure that for a part of each stroke the area of skin being treated is rinsed with clean fluid and that for the remainder of the stroke the fluid and pigments that have collected in the tip 20 during the first part of the stroke are sucked out of it.

The timing of the washing and suction is important in order to continually rinse the needles with fresh solution to remove cellular fluid and pigment and insure that only clean needles penetrate the skin. The timing is illustrated in FIGS. 2A and 2B. On the down stroke (FIG. 2A) inlet hole 34 is lined up with inlet port 24 allowing fluid from the fluid supply container to flow onto needles 30 and the surface of the skin. At the same time outlet hole 32 and outlet port 22 are not aligned so that the source of suction is not connected to the interior of tip 20. On the upstroke (FIG. 2B) as the needles are pulled out of the skin, the alignment of the holes and ports is reversed and the fluid is prevented from entering tip 20 while the suction draws the fluids and pigment out of the tip of the device. By operating in this manner it is seen that, on the one hand, there is an absolute separation between the clean and the "dirty" fluid and, on the other hand, an essentially instantaneous change between the state in which fluid flows into the tip and the state in which it is sucked out of the tip. The "dirty" fluid is sucked from the tip as the needles are withdrawn from the skin in order to minimize the amount of solution that permeates through the holes made by the needles and reaches the cells damaged by the needles inside the dermis. It is important to rinse the needles during each cycle to prevent the transport of pigments and cell material that adhered to the needles during a first cycle back down into the dermis on the next cycle.

A series of experiments were carried out to test the efficacy of the method and in particular the role of the salicylic acid in optimizing the treatment. The following examples are selected from amongst these experiments and are provided merely to illustrate the invention. They are not intended to limit the scope of the invention in any manner.

Experiment 1

Figure 3:
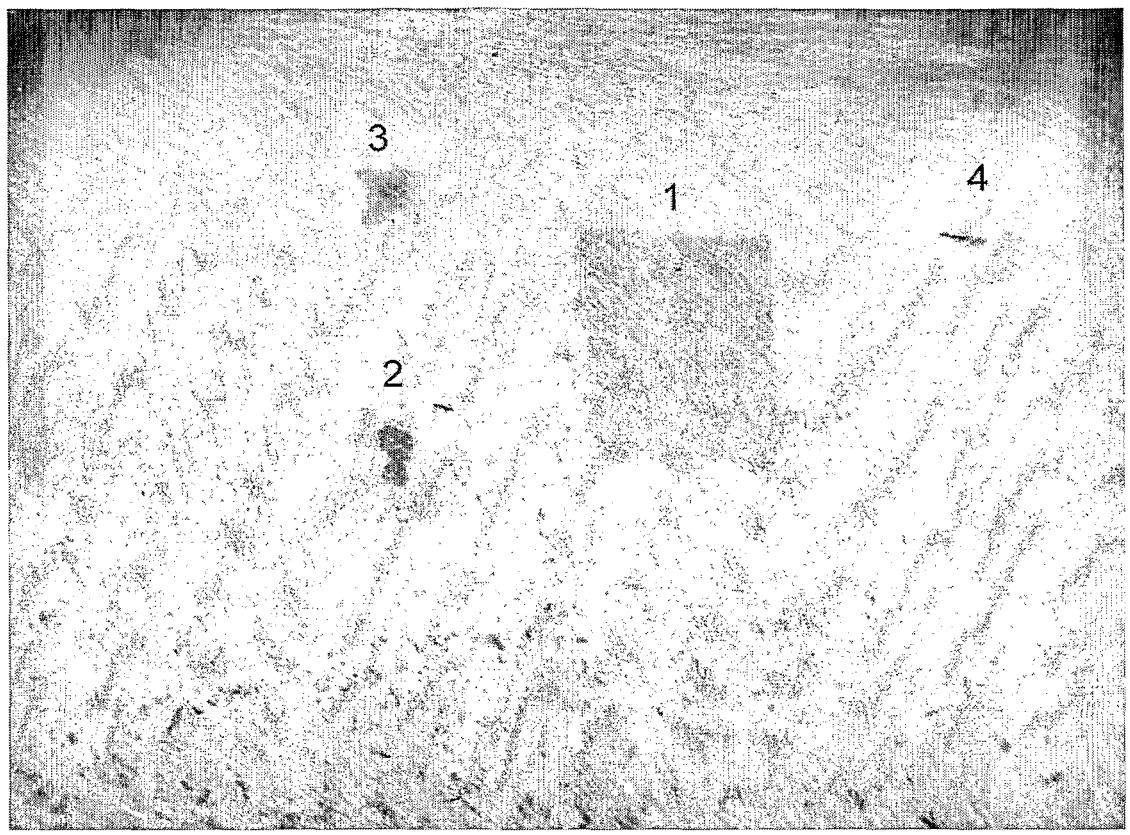
FIG. 3 is a copy of a photograph showing the results of an experiment to remove pigmentation from a tattoo using different types of solutions.
Figure 4A:
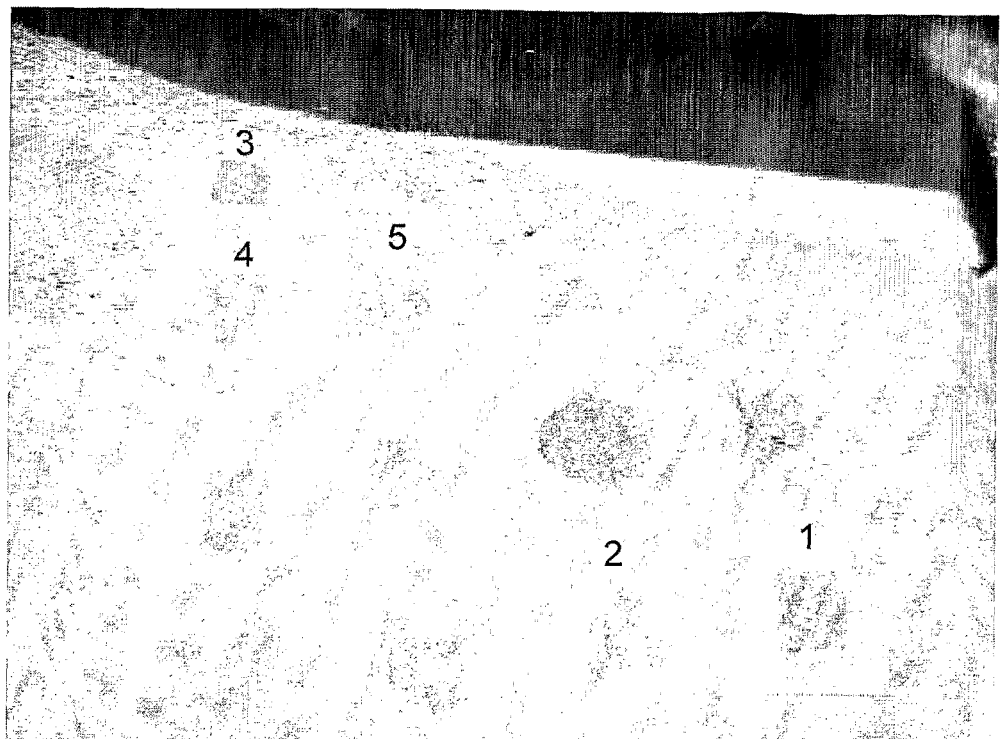
FIGS. 4A and 4B are copies of before and after photographs showing the results of treatment of tattooed areas on the skin of a pig using salicylic acid according to the method of the invention.

A number of tattoos were applied to the skin of a pig. Each of the tattoos was a square having dimensions approximately 1 cm×1 cm filled with a solid blue-grey color. Two months after the tattoos were applied the squares appeared as seen in the photograph reproduced in FIG. 4A. FIG. 3 is a reproduction of a photograph taken 14 days after four of these tattooed areas were treated according to the method of the invention using different types of solution. Square 1 was treated using distilled water and essentially no color reduction was observed. Square 2 was treated using a 2% aqueous solution of salicylic acid. The scar observable in the figure vanished leaving no trace a few days after the photograph was taken and approximately 90% color reduction was observed. Square 3 was treated using a solution containing 17% EDTA. A 60% color reduction was observed but the scar did not vanish. Square 4 was treated with $H_2O_2$ and resulted in a 40-60% reduction in color.

Experiment 2

Figure 4B:
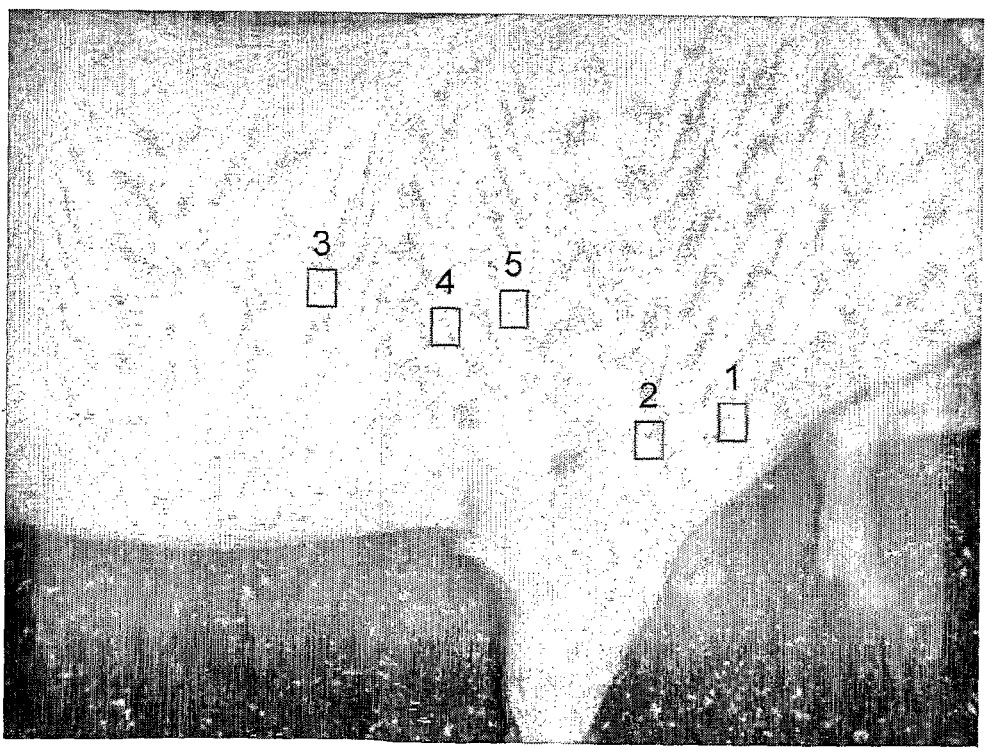

A number of tattoos were applied to the skin of a pig. Each of the tattoos was a square having dimensions approximately 1 cm×1 cm filled with a solid blue-grey color. Two months after the tattoos were applied each of the five squares labeled 1 to 5 on the photograph shown in FIG. 4A was treated according to the method of the invention. The treatment for each square consisted of repeatedly puncturing the skin with the device described hereinabove for three minutes. As the machine was operated, the needles and skin surface were cyclically rinsed with a 5% aqueous solution of salicylic acid. A total of 10 cc of solution was used for each square (i.e. ~10 $cc/cm^2$). Following this initial treatment no further treatment was applied to these five locations. Eighteen days later the photograph shown in FIG. 4B was taken. In this photo it can be seen that all of the original blue-grey color has disappeared and that only traces of squares having a pink color slightly darker than the natural skin color of the pig remain Experiment 3

Figure 5A:
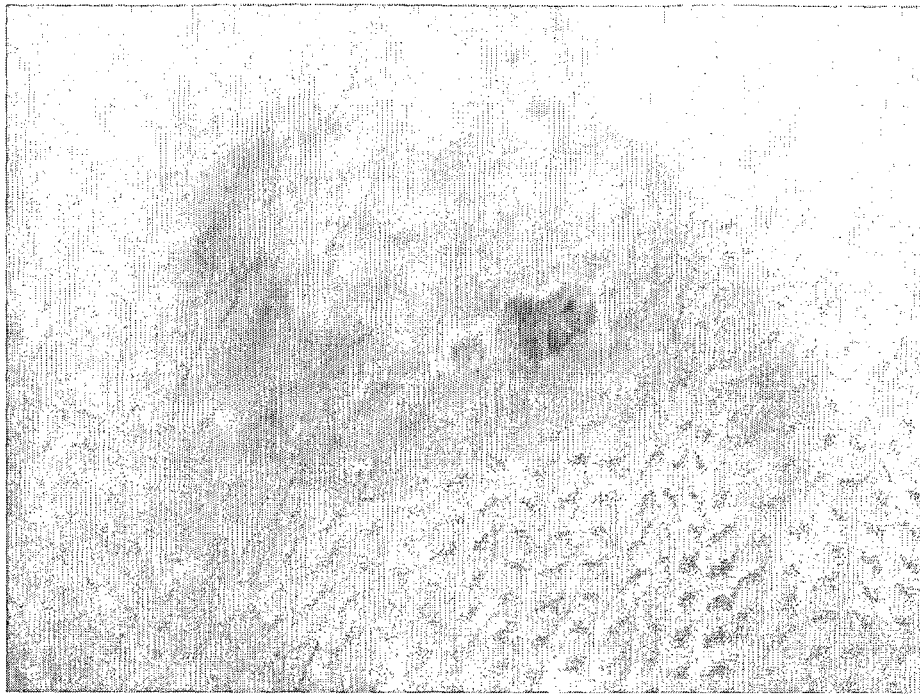
FIGS. 5A and 5B are copies of before and after photographs showing the results of treatment of a pigmented area of skin using salicylic acid according to the method of the invention.
Figure 5B:
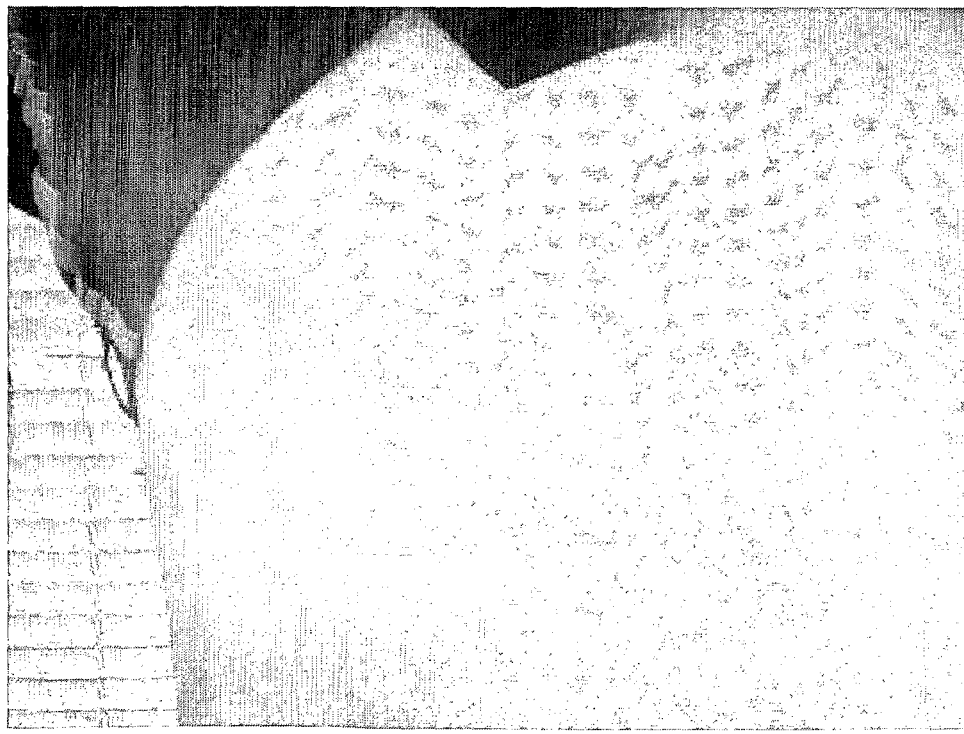

In FIG. 5A is shown a photograph of an area of skin on which there is a reddish-purple pigmented area surrounding brown colored scab. The pigmented area surrounding the scab was treated using the method described above by repeatedly puncturing the skin for ten minutes. During the treatment 10 cc of a 5% aqueous solution of salicylic acid (~10 $cc/cm^2$) was used to clean the needles and surface of the skin. A dry bandage was placed over the treated area for a few days to keep the site clean, but no medication was applied. After this the skin was left unattended. Fourteen days after treatment, during which time the scab dried up and fell off, the photograph shown in FIG. 5B was taken. In FIG. 5B it can clearly be seen that the scar tissue is gone and that the color of the pigmented area has changed to a color slightly greyer than the natural skin color.

Although embodiments of the invention have been described by way of illustration, it will be understood that the invention may be carried out with many variations, modifications, and adaptations, without departing from its spirit or exceeding the scope of the claims.

The invention claimed is:

1. An apparatus adapted for eradicating pigmentation in an area of skin, the apparatus comprising:
    a handle portion including a motor and a gear assembly for causing a reciprocating motion to a shaft connected to the gear assembly;
    a barrel portion surrounding the shaft, a first end of the barrel portion attached to the handle portion and a second end of the barrel portion including a tip configured and arranged to form a hermetic seal with the area of skin;
    an array of needles attached to an end of the shaft near the tip;

an inlet port in the barrel portion, the inlet port connected to solution storage means;
an outlet port in the barrel portion, the outlet port connected to suction means;
a piston attached to the shaft above the array of needles, the piston configured and arranged as a cylindrical valve that is operable to provide a hydraulic seal separating a volume inside the barrel portion above the piston from a volume below the piston and to synchronize opening and closing of the inlet port and the outlet port;
an inlet hole in a side wall of the piston, the inlet hole fluidly connected to a bottom of the piston thereby providing a fluid path from the volume inside the barrel portion below the piston to the inlet hole; and
an outlet hole in a side wall of the piston, the outlet hole fluidly connected to the bottom of the piston thereby providing a fluid path from the volume inside the barrel portion below the piston to the outlet hole;
wherein activation of the motor causes the array of needles to alternatively be pushed out of the tip of the barrel portion to puncture the area of skin to mechanically damage cells containing pigment and to be withdrawn from the area of skin back into the tip, wherein during each downward stroke of the shaft the outlet port is closed by not being lined up with the outlet hole and the inlet port is opened by being lined up with the inlet hole such that solution in the solution storage means flows through the piston into the volume inside the barrel portion below the piston onto the needles thereby rinsing the needles and a surface of the area of skin, wherein during each upward stroke of the shaft the inlet port is closed by not being lined up with the inlet hole and the outlet port is opened by being lined up with the outlet hole thereby allowing solution which flowed onto the surface of the area of skin during the downward stroke and cellular fluids and pigments released by puncturing action of the needles to be sucked through the piston out of the volume inside the barrel portion by the suctioning means, wherein synchronization of opening and closing of the inlet port and the outlet port insures separation of clean and dirty fluid in the tip and minimizes an amount of solution permeating the surface of the area of skin.

2. A method of using the apparatus according to claim 1 comprising:
providing a solution in the solution storage means;
connecting said solution storage means and suction means to the apparatus; and
activating the motor of the apparatus for a predetermined period of time.

3. The method according to claim 2, wherein the solution includes a chemical selected from the group consisting of EDTA, DMSO, Collagenase, Hyaluronidase, Papain, Bromelain hypertonic Saline, Salicylic acid, *Aloe, Bidentis, Kalanchoes, Eucalyptus*, Chamomile, *Calendula, Saliva oficinalis, Helichrysum arenarium*, and Hydrogen peroxide.

4. The method according to claim 3, wherein the solution is an aqueous solution including salicylic acid at a concentration between 2% and 5%.

5. An apparatus for removing skin pigmentation comprising:
a barrel defining a shaft and including a tip configured to create a seal when positioned at a surface area of the skin, the barrel having a handle end and a needle end;
a handle connected to the barrel;
an inlet port within the barrel for introducing a fluid into the shaft;
an outlet port within the barrel for removing the fluid from the shaft;
a valve movable within the shaft between a first position and a second position, the valve configured to enable passage of the fluid from the inlet port to the shaft in the first position and from the shaft to the outlet port in the second position, the valve configured to block the fluid from passing from the inlet port to the shaft in the second position; and
an array of needles provided at the needle end of the shaft and connected to the valve, the needles thereby movable with the valve between the first position and the second position, the needles extending a distance beyond the tip of the barrel at the first position thereby puncturing the area of skin when the tip is positioned at a surface area of the skin while the valve is in fluid communication with the needles thereby applying the fluid to the area of skin during puncturing;
wherein the valve is configured to block the fluid from passing to the outlet port in the first position and the valve includes an inlet hole alignable with the inlet port at the first position but not at the second position, and the valve includes an outlet hole alignable with the outlet port at the second position but not at the first position.

6. The apparatus according to claim 5, further comprising a motor attached to the valve and operable to move the valve between the first position and the second position.

7. The apparatus according to claim 5, the fluid comprising an aqueous solution of salicylic acid.

8. The apparatus according to claim 7, wherein concentration of the salicylic acid in the aqueous solution is between 2% and 5%.

9. The apparatus according to claim 5, wherein the array needles are extendable to puncture into the skin at a depth of 3 mm or less in the first position.

10. The apparatus according to claim 5, wherein the inlet port is arranged relatively closer to the tip of the barrel than the outlet port.

11. The apparatus according to claim 5, the array of needles comprising between 7 needles to 38 needles.

12. A method for eradicating pigmentation in an area of skin, said method comprising repeatedly puncturing said area of skin with an array of needles while rinsing said array of needles with clean solution each time that they puncture said area of skin, said method carried out by:
a) providing an apparatus that comprises:
a handle portion including a motor and a gear assembly for causing a reciprocating motion to a shaft connected to the gear assembly;
a barrel portion surrounding the shaft, a first end of the barrel portion attached to the handle portion and a second end of the barrel portion including a tip configured and arranged to form a hermetic seal with the area of skin;
an array of needles attached to an end of the shaft near the tip;
an inlet port in the barrel portion, the inlet port connected to solution storage means;
an outlet port in the barrel portion, the outlet port connected to suction means;
a piston attached to the shaft above the array of needles, the piston configured and arranged as a cylindrical valve that is operable to provide a hydraulic seal separating a volume inside the barrel portion above the piston from a volume below the piston and to synchronize opening and closing of the inlet port and the outlet port;

an inlet hole in a side wall of the piston, the inlet hole fluidly connected to a bottom of the piston thereby providing a fluid path from the volume inside the barrel portion below the piston to the inlet hole; and an outlet hole in a side wall of the piston, the outlet hole fluidly connected to the bottom of the piston thereby providing a fluid path from the volume inside the barrel portion below the piston to the outlet hole;

b) activating the motor thereby causing the array of needles to alternatively be pushed out of the tip of the barrel portion to puncture the area of skin and to mechanically damage cells containing pigment and to be withdrawn from the area of skin back into the tip, wherein during each downward stroke of the shaft the outlet port is closed by being not lined up with the outlet hole and the inlet port is opened by being lined up with the inlet hole such that solution in the solution storage means flows through the piston into the volume inside the barrel portion below the piston onto the needles thereby rinsing the needles and a surface of the area of skin, wherein during each upward stroke of the shaft the inlet port is closed by not being lined up with the inlet hole and the outlet port is opened by being lined up with the outlet hole thereby allowing solution which flowed onto the surface of the area of skin during the downward stroke and cellular fluids and pigments released by puncturing action of the needles to be sucked through the piston out of the volume inside the barrel portion by the suctioning means.

13. The method according to claim 12, wherein the solution is an aqueous solution of salicylic acid having a concentration of between 2% and 5%.

14. The method according to claim 13, wherein duration of the puncturing of the area of skin and applying of the aqueous solution of salicylic acid is no longer than thirty minutes.

15. The method according to claim 12, wherein the pigmentation is from a tattoo.

16. The method according to claim 12, wherein the pigmentation is due to a natural process.

17. The method according to claim 16, wherein the natural process is selected from the group consisting of healing of wounds, freckles, age spots, and birth marks.

18. The method according to claim 12, wherein the needles puncture the skin to a depth of 3 mm or less.

* * * * *